US012678258B2

(12) United States Patent
Kimpton et al.

(10) Patent No.: US 12,678,258 B2
(45) Date of Patent: *Jul. 14, 2026

(54) DRAPE INTERFACE STRUCTURE

(71) Applicant: CMR Surgical Limited, Cambridge (GB)

(72) Inventors: Laura Saranne Kimpton, Baldock (GB); Thomas Edward Parker, London (GB); Merissa Lim Sarrias, Hauxton (GB)

(73) Assignee: CMR Surgical Limited, Cambridge (GB)

( * ) Notice: Subject to any disclaimer, the term of this patent is extended or adjusted under 35 U.S.C. 154(b) by 180 days.

This patent is subject to a terminal disclaimer.

(21) Appl. No.: 18/472,671

(22) Filed: Sep. 22, 2023

(65) Prior Publication Data

US 2024/0099803 A1 Mar. 28, 2024

(30) Foreign Application Priority Data

Sep. 23, 2022 (GB) ...................................... 2213923

(51) Int. Cl.
*A61B 90/00* (2016.01)

(52) U.S. Cl.
CPC ...... *A61B 90/08* (2016.02); *A61B 2090/0813* (2016.02)

(58) Field of Classification Search
CPC .......... B24J 19/00; A61B 34/30; A61B 34/00; A61B 34/70; A61B 1/00135; A61B 1/00142; A61B 2090/0813; A61B 90/08; A61B 46/00; A61B 46/10; A61B 46/23; A61B 17/00

USPC ...... 700/245; 901/49–50; 600/121, 124–125; 606/130; 128/849–856
See application file for complete search history.

(56) References Cited

U.S. PATENT DOCUMENTS

| | | | |
|---|---|---|---|
| 2009/0248039 A1 | 10/2009 | Cooper et al. | |
| 2024/0099798 A1* | 3/2024 | Kimpton | ................ A61B 46/10 |

FOREIGN PATENT DOCUMENTS

| | | | | |
|---|---|---|---|---|
| GB | 2538230 A | 11/2016 | | |
| GB | 2570518 A * | 7/2019 | ............. | A61B 46/10 |
| WO | WO-2012078620 A2 * | 6/2012 | ............. | A61B 46/00 |
| WO | WO-2014005689 A2 * | 1/2014 | ............. | A61B 17/00 |
| WO | 2016081286 A1 | 5/2016 | | |
| WO | WO-2018141783 A1 * | 8/2018 | ........ | A61M 25/0009 |

OTHER PUBLICATIONS

WO 2014005689 machine translation (Year: 2014).*
WO 2018141783 A1 machine translation (Year: 2018).*
Search Report Under Section 17 for UK Patent Application No. GB2213923.2, mailed Feb. 23, 2023.

* cited by examiner

*Primary Examiner* — Caitlin A Carreiro
(74) *Attorney, Agent, or Firm* — Andrus Intellectual Property Law, LLP

(57) ABSTRACT

A drape interface structure including a rigid frame defining an opening, a membrane spanning the opening of the frame, and a drive transfer element attached to the membrane and adapted to convey motion through the membrane. The membrane includes a first region of a first elastic deformability and a second region of a second elastic deformability different from the first elastic deformability.

19 Claims, 9 Drawing Sheets

DRAPE INTERFACE STRUCTURE

CROSS-REFERENCE TO RELATED APPLICATION

This application claims priority to GB Patent Application No. 2213923.2, filed Sep. 23, 2022, which is incorporated herein by reference in its entirety.

FIELD OF THE DISCLOSURE

This invention relates to an interface structure which provides a sterile barrier. In one embodiment, the structure has a thin membrane, retained in a rigid frame and covering an opening defined by the frame. At least part of the membrane may elastically deform without tearing or detaching from the frame, meaning that a barrier is maintained, and no contaminants can pass through. The interface structure may have at least one drive transfer element retained in the membrane. Each drive transfer element may be adapted to convey motion through the structure.

BACKGROUND

In a surgical environment, it is particularly important that any components that cannot readily be disinfected between procedures are prevented from becoming contaminated during an operation.

Robots have become increasingly prevalent for use in surgical procedures. A surgical robotic assembly comprises a base which supports the robot, an arm and an instrument. The arm extends between the base and instrument. There is an interface between the instrument and the arm; at this interface, various instruments can be releasably connected to the arm and a driving mechanism in the arm can be used to manipulate the distal end of the instrument.

It is typically impractical to sterilise the base and arm of a robotic assembly without damaging the mechanical components and the large size presents further challenges when disinfecting and sterilising. As an alternative to disinfection and sterilisation, covering a surgical robot with a disposable covering is an effective barrier to prevent contamination. A surgical drape is a covering which envelops the base and arm of a surgical robot to separate a sterile field from an operative area where surgery is performed by the instrument.

At the interface between the robotic arm and instrument, the two components can suitably engage with each other so that the instrument is supported and can articulate to perform or assist with a surgical procedure. There is a need for an improved interface structure which can convey motion from the robotic arm to the instrument through a barrier during a surgical procedure while maintaining sterility.

SUMMARY OF THE INVENTION

According to a first aspect of the present invention there is provided a drape interface structure comprising: a membrane spanning the opening of the frame, and a drive transfer element attached to the membrane and adapted to convey motion through the membrane. The membrane spanning the opening may comprise a first region of a first elastic deformability and a second region of a second elastic deformability different from the first elastic deformability.

The first region may comprise a less deformable region and the second region comprises a more deformable region such that, in response to movement of the drive transfer element, the more deformable region preferentially elastically deforms over the less deformable region.

The more deformable region and the less deformable region may be arranged so as to apply less resistance to the movement of the drive transfer element in a direction along a drive path of the drive transfer element than in a direction not along the drive path.

The more deformable region and the less deformable region may be arranged so as to apply the lowest resistance to the movement of the drive transfer element in a direction along the drive path.

The more deformable region and the less deformable region may be adjacent.

The less deformable region may be thicker than the more deformable region.

The less deformable region may comprise a portion attached to the surface of the membrane.

The less deformable region may comprise a thicker region of the membrane material than the more deformable region.

The less deformable region may have a greater stiffness than the more deformable region.

The less deformable region may comprise a material with a greater stiffness than the material of the more deformable region.

The more deformable region may enclose the drive transfer element. The less deformable region may enclose the more deformable region.

The less deformable region may be enclosed by a further more deformable region. The further more deformable region may be at least partially enclosed by a further less deformable region.

A plurality of less deformable regions may at least partially surround the drive transfer element. The plurality of less deformable regions and the drive transfer element may be separated by the more deformable region.

The plurality of less deformable regions may be arranged in a hexagonal pattern.

The more deformable region may comprise a corrugated structure at least partially surrounding the drive transfer element. The corrugated structure may be enclosed by the less deformable region.

The corrugated structure may comprise further less deformable regions arranged within the corrugated structure.

The drape interface structure may comprise one or more further drive transfer elements. Each further drive transfer element may be attached to the membrane and adapted to convey motion through the membrane.

The one or more further drive transfer elements may be adapted to convey motion through the membrane along respective drive paths. The respective drive paths of the drive transfer elements may be parallel to one another.

The more deformable region and the less deformable region may be arranged so as to apply less resistance to the movement of each of the drive transfer elements in a direction along a respective drive path of each drive transfer element than in a direction not along the respective drive path.

The more deformable region and the less deformable region may be arranged so as to apply the lowest resistance to the movement of each of the drive transfer elements in a direction along the respective drive path.

The drive transfer element may comprise a recess on a first side of the membrane and a protrusion on the second side of the membrane.

The drive transfer element recess may be engageable with an interface protrusion. The drive transfer element protrusion may be engageable with an interface recess.

The frame may comprise a securing fitting for securing the frame to a robot arm.

The drive path of the drive transfer element may be linear.

The rigid frame may be heat welded to the membrane. The drive transfer element may be heat welded to the membrane.

The material of the membrane may be a thermoplastic polymer.

The thermoplastic polymer material of the membrane may comprise one or more of high-density polyethylene or linear low-density polyethylene.

The material of the one or more drive transfer elements may comprise a non-elastomeric material.

The material of the one or more drive transfer elements may comprise polyethylene.

The material of the frame may comprise polyethylene.

DETAILED DESCRIPTION

The following description is presented to enable any person skilled in the art to make and use the invention, and is provided in the context of a particular application. Various modifications to the disclosed embodiments will be readily apparent to those skilled in the art.

Figure 1:
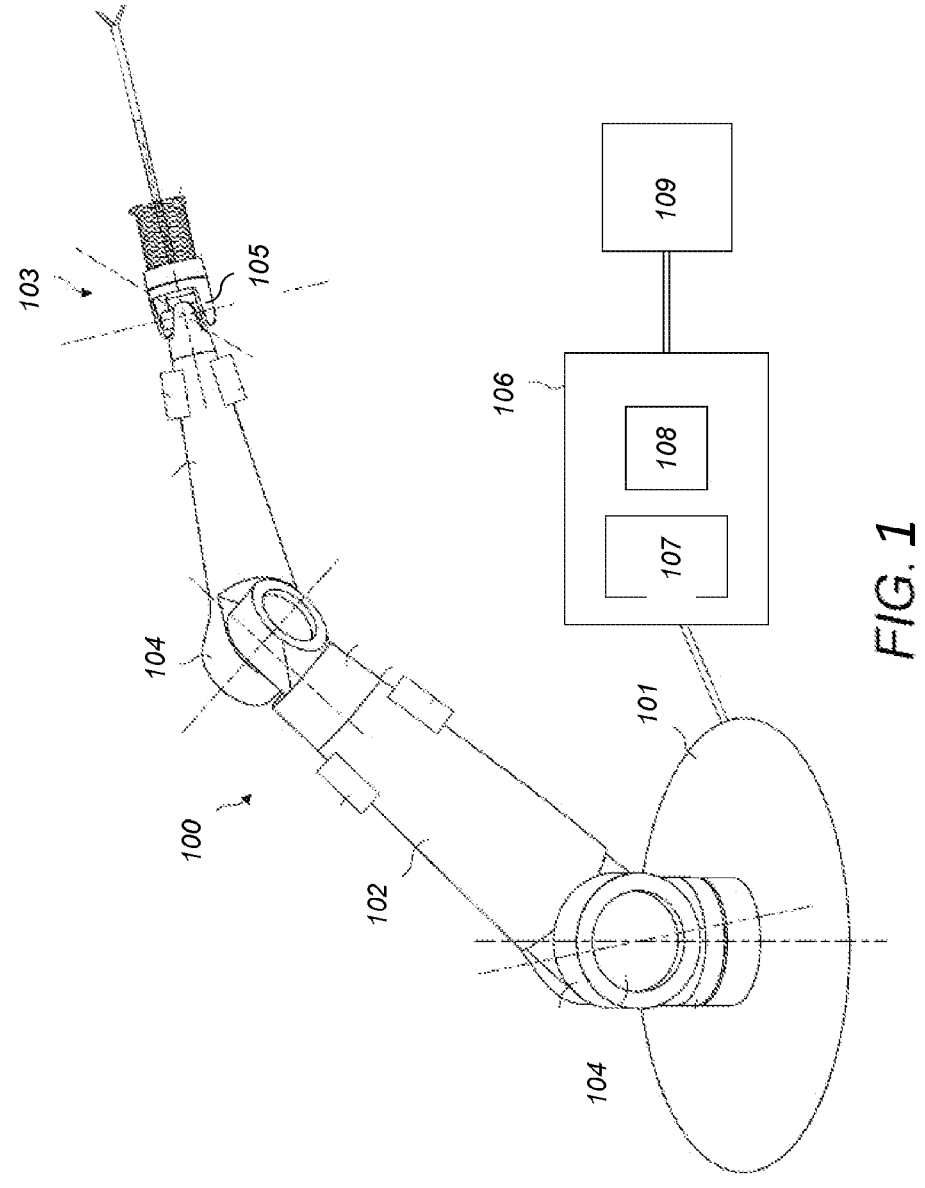
FIG. 1 illustrates a surgical robot and associated control system.

FIG. 1 shows a typical surgical robot 100 and associated control system 106. A base 101 is shown which supports an arm 102 and an instrument 103. The base provides stability by, for example, being rigidly attached to an operating theatre floor or attached to a trolley. The arm 102 is articulated by means of multiple flexible joints 104 along its length, used to position the instrument 103 in a suitable location for performing surgery. A surgical drape (not shown) may be attached at the interface 105 between the instrument 103 and arm 100. The surgical instrument 103 is connected at the distal end of the robot arm 102, it may be releasably attached.

The control system 106 includes a surgeon command interface 109 where commands are input. The control system 106 comprises a processor 107 and a memory 108. The control system 106 is coupled to motors for driving motion of a drive assembly to articulate the instrument 103.

Figure 2:
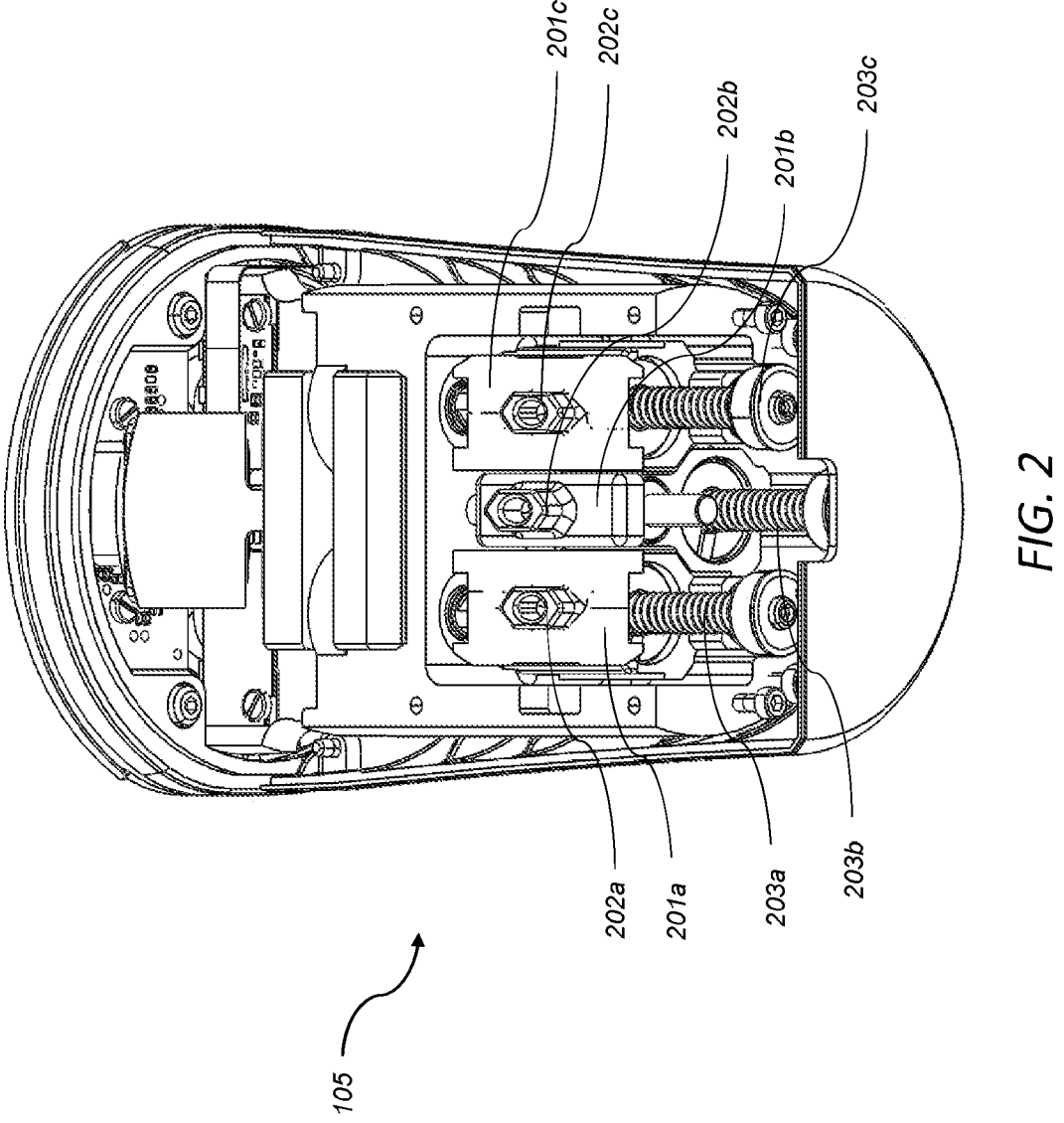
FIG. 2 illustrates the interface of a surgical robot arm.

A surgical robot arm 102 interface 105 is illustrated in FIG. 2. The interface 105 comprises one or more robot arm interface elements 201. FIG. 2 shows three robot arm interface elements 201a, 201b, 201c. However, it will be appreciated that there may be a different number of robot arm interface elements 201a, 201b, 201c depending on the requirements on the driving structure. For example, the number of degrees of freedom of the instrument 103 may determine the number of drive inputs required which may in turn determine the number of robot arm interface elements 201a, 201b, 201c.

The robot arm interface elements 201a, 201b, 201c are shown to comprise interface features 202a, 202b, 202c. The robot arm interface features 202a, 202b, 202c are suitable for engaging with corresponding features in the instrument 103. FIG. 2 shows that the robot arm interface features 202a, 202b, 202c comprise interface protrusions 202a, 202b, 202c. However, it will be appreciated that the robot arm interface features 202a, 202b, 202c may additionally or alternatively comprise interface recesses 202a, 202b, 202c. The selection of a protrusion or recess may depend on the requirements of the drive system, and the features present in the instrument 103. The robot arm interface features 202a, 202b, 202c are located on the robot arm interface elements 201a, 201b, 201c. For example, the robot arm interface features 202a, 202b, 202c may extend out of, for protrusions, or extend into, for recesses, the robot arm interface elements 201a, 201b, 201c.

In FIG. 2, the robot arm interface elements 201a, 201b, 201c are driven by respective lead screws 203a, 203b, 203c. The lead screws 203a, 203b, 203c may rotate along a female threaded elements engaged with the lead screws 203a, 203b, 203c. This causes the female threaded elements to move along the lead screws 203a, 203b, 203c. The result is that the lead screws 203a, 203b, 203c may provide the robot arm interface elements 201a, 201b, 201c with linear drive. However, it will be appreciated that there may be different ways of driving the robot arm interface elements 201a, 201b, 201c, which may result in different types of drive. For example, the robot arm interface elements 201a, 201b, 201c may be provided with rotational or irregular non-linear drive.

Figure 3:
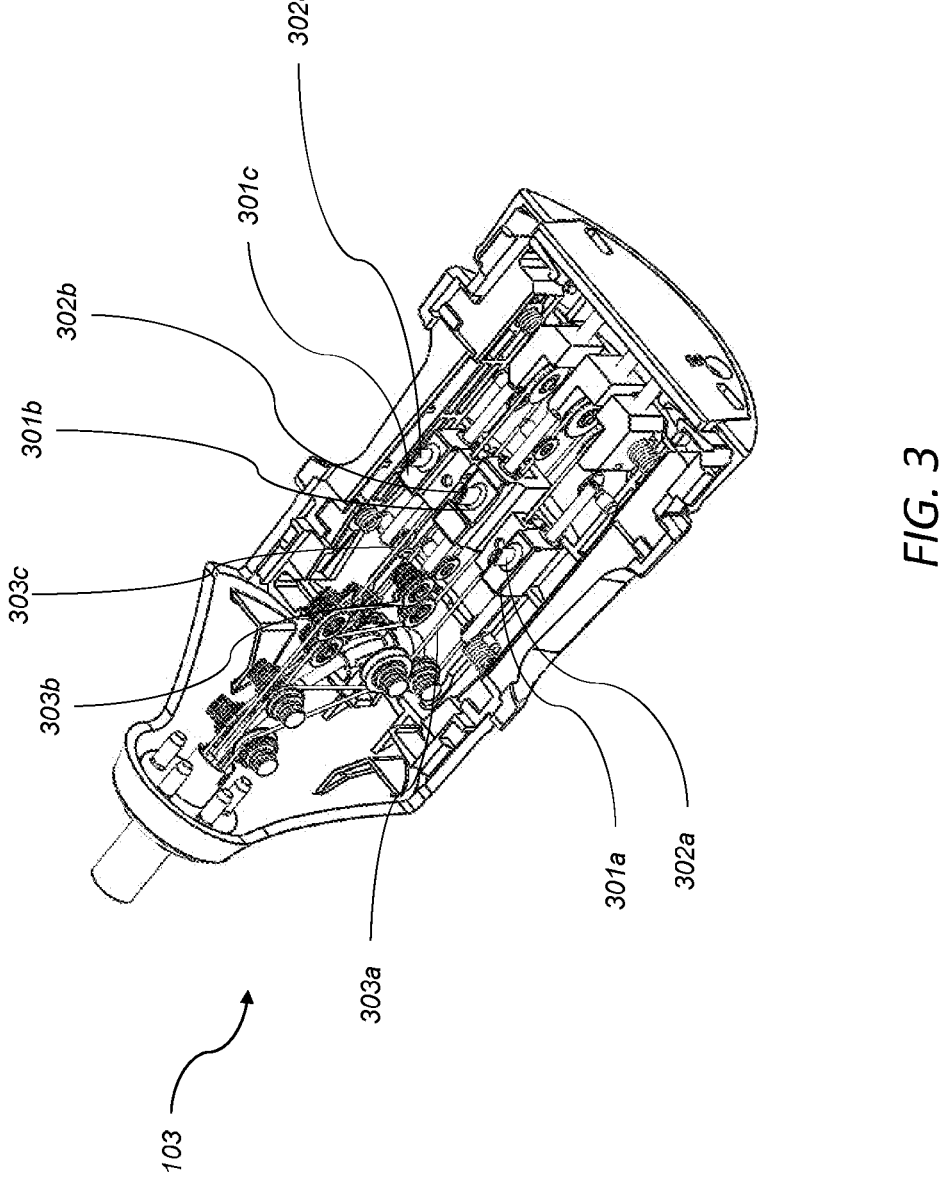
FIG. 3 illustrates the interface of a surgical instrument.

A surgical instrument 103 is illustrated in FIG. 3. The instrument 103 comprises one or more instrument interface elements 301. FIG. 3 shows three instrument elements 301a, 301b, 301c. However, it will be appreciated that there may be a different number of instrument elements 301a, 301b, 301c depending on the requirements on the driving structure. For example, the number of degrees of freedom of the instrument 103 may determine the number of drive inputs required which may in turn determine the number of instrument interface elements 301a, 301b, 301c.

The instrument interface elements 301a, 301b, 301c are shown to comprise interface features 302a, 302b, 302c. The instrument interface features 302a, 302b, 302c are suitable for engaging with corresponding features in the robot arm 102. FIG. 3 shows that the instrument interface features 302a, 302b, 302c comprise interface protrusions 302a, 302b, 302c. However, it will be appreciated that the instrument interface features 302a, 302b, 302c may additionally or alternatively comprise interface recesses 302a, 302b, 302c. The selection of a protrusion or recess may depend on the requirements of the drive system, and the features present in the robot arm 102. The instrument interface features 302a, 302b, 302c are located on the instrument interface elements 301a, 301b, 301c. For example, the instrument interface features 302a, 302b, 302c may extend out of, for protrusions, or extend into, for recesses, the instrument interface elements 301a, 301b, 301c.

In FIG. 3, the instrument interface elements 301a, 301b, 301c drive instrument cables 303a, 303b, 303c. The instrument interface elements 301a, 301b, 301c are connected to the instrument cables 303a, 303b, 303c and slide along straight bars. The result is that the instrument interface elements 301a, 301b, 301c may provide the instrument cables 303*a*, 303*b*, 303*c* with linear drive. However, it will be appreciated that there may be different ways of driving the instrument cables 303*a*, 303*b*, 303*c*, which may result in different types of drive. For example, the instrument cables 303*a*, 303*b*, 303*c* may be provided with rotational or irregular non-linear drive. The instrument cables 303*a*, 303*b*, 303*c* are used to control the end effector elements of the instrument 103.

Figure 4:
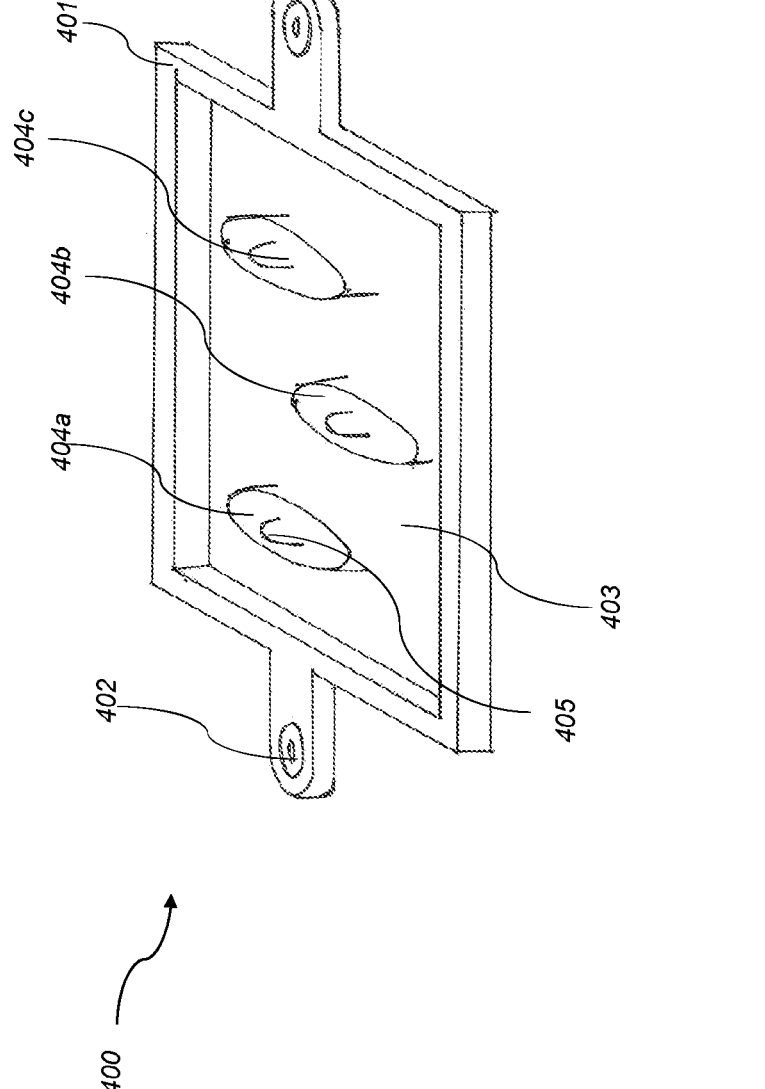
FIG. 4 illustrates a perspective view of a drape interface structure.
Figure 5:
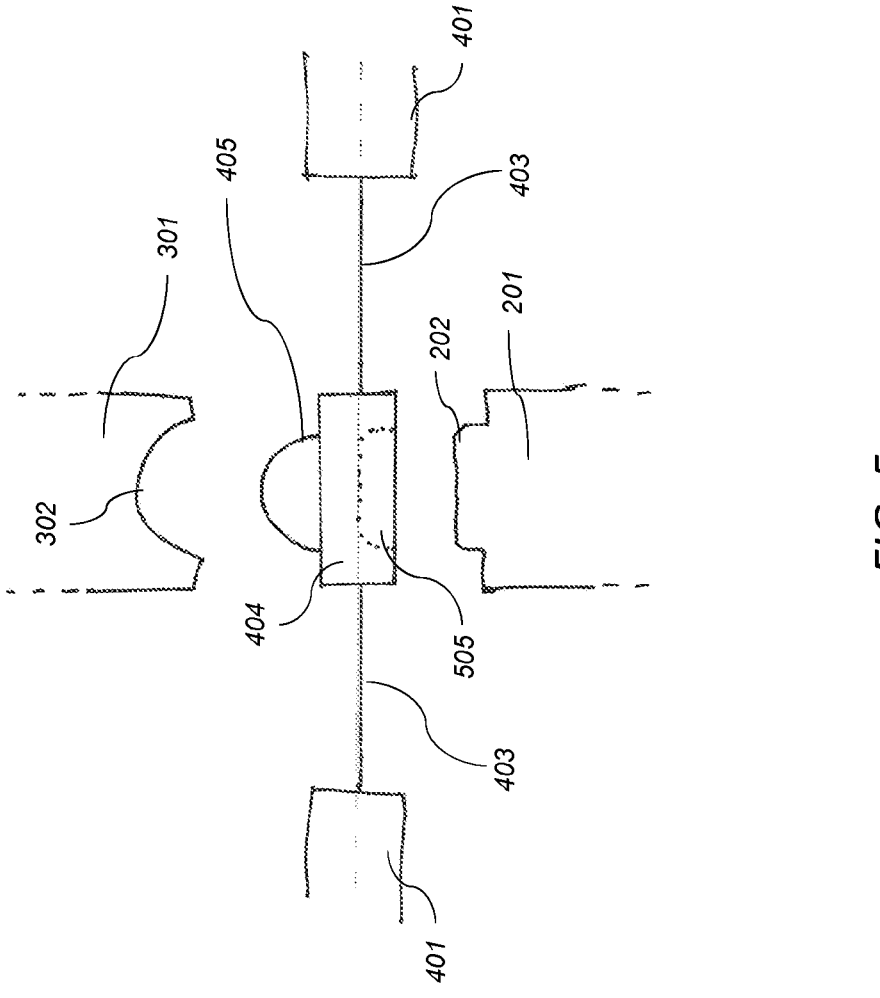
FIG. 5 illustrates a cross-sectional view of a drive transfer element.

A drape interface structure of all embodiments is illustrated in FIGS. 4 and 5.

FIG. 4 shows the drape interface structure 400. The drape interface structure 400*a* comprises a frame 401. As shown in FIG. 4, the frame 401 comprises a substantially rectangular profile. However, other shapes for the frame 401 may be suitable, such as round shapes. Additionally, the edges of the frame 401 may be chamfered, rounded, or notched. In any event, the frame 401 preferably is shaped to fit with the structure to which it is attached. The frame 401 may also be a rigid frame. In other words, the frame 401 may substantially maintain its shape when under loading during operation. Alternatively, the frame 401 may not be a rigid frame. For example, the frame 401 may be provided by a drape surrounding the drape interface structure 400.

The frame 401 may comprise a non-elastomeric material. In this way, the frame 401 may comprise the rigid structure which may substantially maintain its shape when under loading during operation. In particular, the frame 401 may comprise a polyolefin material, such as polyethylene or polypropylene. Additionally, the frame 401 may be made from more than one material. For example, the frame 401 may be made from high density polyethylene (HDPE) with a styrene-ethylene-butylene-styrene (SEBS) coating.

The outer edge of the frame 401 (the sides opposing the opening) may be attached to a surgical drape (not shown in the Figures). This surgical drape may be used to cover at least the arm 102 of the surgical robot 100. The drape interface structure 400 may be retained within the drape or connect to it. In an embodiment, the surgical drape is attached to the drape interface structure 400. A technician, surgeon or nurse may position the drape interface structure 400 between the robotic arm 102 and robotic instrument 103 prior to a surgical procedure. The drape interface structure 400 may be disconnected after a surgical procedure.

The frame 401 defines an opening. As shown in FIG. 4, the opening is substantially rectangular. However, other shapes for the frame 401 may be suitable, such as round shapes. The opening is covered by a membrane 403. The membrane 403 spans the opening of the frame 401. In particular, the membrane 403 spans the full area of the opening such that there is a sterile barrier formed.

The membrane 403 may be heat welded to the frame 401. The membrane 403 may be chemically bonded to the frame 401, for example with adhesive. The membrane 403 may comprise a thermoplastic polymer. The membrane may comprise polyethylene. The membrane may comprise an aligned polymer film. In particular, the membrane 403 may comprise high-density polyethylene. Alternatively, or in addition, the membrane 403 may comprise linear low-density polyethylene. A single material or a combination of materials may be used in the membrane 403 to give the desired properties.

Thermoplastics are capable of being heated to a softened state and reshaped. Thermoplastic components may be well-suited to repeated processing and thermal attachment to other components. Several versatile manufacturing methods are commonly used to process thermoplastics such as injection moulding, blow moulding, and casting. Thermoplastic sheets are produced industrially by first blending the necessary raw materials, then heating and pressing through an extrusion die, then the extruded plastic is drawn into a sheet by the pressure applied between rollers. Several sets of rollers or multiple passes through rollers may be used to draw the sheet to a specific thickness while the thermoplastic is warm. Finally, the sheet is cooled and can then be cut to a desired size and shape.

Polyethylenes are a group of polymers with the chemical formula $(C_2H_4)_n$ as the repeat unit. The mechanical properties of polyethylene are influenced by the molecular weight and the extent of branching; highly branched polyethylene has a higher density and typically has a higher percentage crystallinity, meaning it is typically more brittle.

HDPE is made up of linear chains with less branching than the short branches in linear low density polyethylene (LLDPE). Puncture-resistant thin films of LLDPE are readily processed. LLDPE has a structure composed of many short, branched chains, these branches have a low degree of cross linking between the chains so, in response to an applied tensile stress, the chains are free to slide over each other without becoming entangled. LLDPE has a low dispersity (a narrow distribution of molecular weight) so a higher degree of crystallinity can be achieved. LLDPE has similar strength to HDPE but is more flexible. Use of LLDPE for the material of the membrane 403 may provide good strength and flexibility.

The membrane 403 may have a thickness of less than 1 mm. The elongation at break of the film may be more than 600%. The density of the film at room temperature may be 0.97 g/cm$^3$ plus or minus 10% The elongation at break of the film may be more than 400%. If the film is an aligned film the elongation at break may be 1400% or more in the alignment direction The frame 401 comprises securing fittings 402 for securing the frame 401 to a structure. Preferably, the securing fittings 402 are capable of securing the frame 401 to the robot arm 102. In particular, the securing fittings 402 are capable of securing the frame 401 to the interface 105 of the robot arm 102. The securing fittings 402 may comprise a click-in lock, magnets, screws or any other suitable types of securing fittings 402. The securing fittings 402 are capable of engaging with a corresponding feature on the robot arm 102. The securing fittings 402 may be a surface relief. As shown in FIG. 4, the securing fittings 402 are positioned on a fin which extends away from the opening of the frame 401. There may be more than one securing fittings 402. FIG. 4 shows two securing fittings 402 which are located on opposite sides of the frame 401. However, the number, and location, of securing fittings 402 may be varied depending on the force requirements on the securing fittings 402. An operator, prior to a procedure, can position the frame 401 to releasably attach to an arm 102 and on the opposing side of the frame 401 releasably attach to an instrument 103.

As shown in FIG. 4, the drape interface structure 400 comprises a drive transfer element 404. The drive transfer element 404 is attached to the membrane 403. In other words, the drive transfer element 404 may be a separate component to the membrane 403 and attached thereto. The drive transfer element 404 may be heat welded to the membrane 403. The drive transfer element 404 may be chemically bonded to the membrane 403, for example with adhesive. The membrane 403 may be formed from a flat sheet with holes cut out such that the membrane 403 is attached to the sides of the drive transfer element 404. Alternatively, the flat sheet of the membrane 403 could be bonded to the top or bottom surface of the drive transfer element 404. Alternatively, the membrane 403 may be over moulded to the drive transfer element 404. The membrane 403 may be substantially taught. In this way, the drive transfer element 404 may be held in the membrane 404.

In an alternative embodiment, the membrane 403 may be joined to the frame 401 and drive transfer element 404 by laser welding. In a further alternative embodiment, the membrane 403 may have a backing film which is adhered to a surface of the membrane 403 to improve the bonding with the rigid parts and reinforce the membrane 403. Lamination of polymer layers may be used to form a membrane 403.

The drape interface structure 400 may further comprise a reinforcement member in the membrane 403. The reinforcement member may be adjacent to the drive transfer element 404. For example, the reinforcement member may comprise a ring which surrounds the drive transfer element 404. The reinforcement member may comprise a different material to the membrane 403. The reinforcement member may comprise a stiffer and/or stronger material than the membrane 403. The reinforcement member may provide additional strength to the membrane 403 in the region where the membrane 403 and the drive transfer element 404 connect. In a region of the membrane 403 surrounding the drive transfer element 404 the shear forces may be higher. In this way, the reinforcement member may reduce the likelihood of tearing of the membrane 403 in the region surrounding the drive transfer element 404.

Polyethylene (PE), which as described herein the membrane 403 may be manufactured from, is non-polar and may not readily react with solvents, meaning that adhesives and solvents may not be appropriate for joining PE parts to each other. Heat welding of PE parts is a simple and effective method of joining, which involves overlaying the parts to be attached and applying heat to soften the thermoplastic. An infrared emitter may be used to weld the membrane to the frame 401 and the drive transfer element 404. The thin membrane layer is suited to attachment by heat welding because it transmits heat well and melts to bond to a substrate. The strength of an attachment made by heat welding parts varies with the temperature used and the materials selected. A higher seal initiation temperature is needed for HDPE than LLDPE: HDPE melts in the temperature range 126° C. to 135° C., LLDPE melts in temperature range 115° C. to 160° C. In this way, an LLDPE membrane 403 may have a lower seal initiation temperature.

The heat welding process fixes the membrane 403 to the rigid parts and a barrier to contaminants is produced. The frame 401 and drive transfer elements 404*a*, 404*b*, 404*c* may be made of the same material, for example a polymer, metal, or composite. The frame 401 and the drive transfer element 404 may be made of dissimilar materials. A non-elastomer such as PE may be used to form the rigid parts.

The drive transfer element 404 is adapted to convey motion through the membrane 403. The drive transfer element 404 may move with respect to the frame 401 in the membrane 403. The membrane 403 may be flexible such that the drive transfer element 404 may move within the opening of the frame 401.

The drive transfer element 404 may move along a drive path. The drive path may be a linear path. The drive path may be a circular path. The drive path may be irregular with linear and curved sections. In this case of linear drive paths, the drive path may follow a drive axis. The drive path may be determined by the structure that is driving the drive transfer element 404. The drive transfer element 404 may also convey rotational motion through the membrane 403. In this example, the drive transfer element 404 may not move along a drive path. Instead, the drive transfer element 404 may rotate around the stationary point. In another embodiment, the drive transfer element 404 may both rotate and travel along a drive path 404, such that the point of rotation also moves.

As shown in more detail in FIG. 5, the drive transfer element 404 may comprise a recess 505 on a first side of the membrane 203. In particular, the drive transfer element recess 505 may be engageable with an interface protrusion 202. The first side of the membrane 403 may, for example, face the robot arm 102. In this case, the interface protrusion 202 is located on an interfacing element 201 of the robot arm 102. Alternatively, the first side of the membrane 403 may face the instrument 103. In this case, the interface protrusion 202 is located on an interfacing element 201 of the instrument 103. As shown in FIG. 5, the drive transfer element recess 505 may comprise a concave or semi-circular shape. In 3D this may provide a hemispherical recess. The interface protrusion 202 may comprise a corresponding shape, for example the convex or semi-circular shape. In 3D this may provide a hemispherical protrusion. This curved shape, or any other form of tapered shape, may provide self-locating when the interface protrusion 202 is engaged with the drive transfer element recess 505. However, it will be appreciated that other shapes may be suitable depending on the locating and loading requirements on the drive structure. For example, the drive transfer element recess 505 may comprise a pyramid shape, a rectangular shape, or a cylindrical shape. It is preferable that the shape of the drive transfer element recess 505 and the interface protrusion 202 correspond to one another. In other words, the interface protrusion 202 should fit in the drive transfer element recess 505. Preferably, the fit between the interface protrusion 202 and the drive transfer element 505 should be a snug, or an interference fit.

The drive transfer element 404 may comprise a protrusion 405 on a second side of the membrane 403. In particular, the drive transfer element protrusion 405 may be engageable with an interface recess 302. The second side of the membrane 403 may, for example, face the instrument 103. In this case, the interface recess 302 is located on an interfacing element 301 of the instrument 103. Alternatively, the second side of the membrane 403 may face the robot arm 102. In this case, the interface recess 302 is located on an interfacing element 301 of the robot arm 102. As shown in FIG. 5, the drive transfer element protrusion 405 may comprise a convex or semi-circular shape. In 3D this may provide a hemispherical protrusion. The interface recess 302 may comprise a corresponding shape, for example the concave or semi-circular shape. In 3D this may provide a hemispherical recess. This curved shape, or any other form of tapered shape, may provide self-locating when the drive transfer element protrusion 405 is engaged with the interface recess 302. However, it will be appreciated that other shapes may be suitable depending on the locating and loading requirements on the drive structure. For example, the drive transfer element protrusion 405 may comprise a pyramid shape, a rectangular shape, or a cylindrical shape. It is preferable that the shape of the interface recess 302 and the drive transfer element protrusion 405 correspond to one another. In other words, the drive transfer element protrusion 405 should fit in the interface recess 302. Preferably, the fit between the drive transfer element protrusion 405 and interface recess 302 should be a snug, or an interference fit.

In alternative embodiments, the drive transfer element 404 may comprise a recess 505 on both sides of the membrane 403, or the drive transfer element 404 may comprise a protrusion 405 on both sides of the membrane 403. In any event, the drive transfer element 404 may be provided with a suitable number and arrangement of recesses 505 and protrusions 405 depending on the structure of the robot arm 102 and instrument 103 on either side of the drive transfer element 404.

The drive transfer element 404 may comprise a non-elastomeric material. The material properties of the drive transfer element 404 may be stiffer than the membrane 403. In this way, the drive transfer element 404 may comprise the rigid structure which may substantially maintain its shape when under loading during operation. In particular, the drive transfer element 404 may comprise a polyethylene material. The drive transfer element 403 may comprise more than one material. For example, the drive transfer element 403 may comprise a stiffer core and a less stiff coating. In this way, the core may provide the rigid structure, and the coating may provide good adhering properties for connecting to other components. The drive transfer element 404 may be formed by moulding, casting and/or milling. In the case of milling, CNC milling may be used to form the drive transfer element protrusion 406 and/or drive transfer element recess 405.

As shown in FIG. 4, the drape interface structure 400 may comprise more than one drive transfer element 404. FIG. 4 shows three drive transfer elements 404a, 404b, 404c. It will be appreciated that there may be a different number of drive transfer elements 404a, 404b, 404c depending on the requirements on the driving structure. Each of the drive transfer elements 404a, 404b, 404c are attached to the membrane 403. Each of the drive transfer elements 404a, 404b, 404c may be heat welded to the membrane 403.

As seen in FIG. 4, the opening of the frame defines a window in a notional coordinate system where the opening extends in the x and y directions. The area of the window is relatively larger than the drive transfer elements 404a, 404b, 404c, such that a plurality of drive transfer elements 404a, 404b, 404c can fit within the window. A section of membrane 403 cut from a larger sheet has an area at least the size of the window, and may have an excess edge to attach to the frame. In the coordinate system, the motion of the drive transfer elements 404a, 404b, 404c may be a translation in the x, y, z direction, or some combination of these, the motion may also be a rotation.

Each of the drive transfer elements 404a, 404b, 404c are adapted to convey motion through the membrane 403. Each of the drive transfer elements 404a, 404b, 404c may move with respect to the frame 401 in the membrane 403. Each of the drive transfer elements 404a, 404b, 404c may move independently with respect to one another. The membrane 403 may be flexible such that each of the drive transfer elements 404a, 404b, 404c may move within the opening of the frame 401.

Each of the drive transfer elements 404a, 404b, 404c may move along a respective drive path. The respective drive paths may be a linear path. The respective drive paths may be circular paths. The respective drive paths may be irregular with linear and curved sections. In this case of linear drive paths, the drive path may follow a drive axis. The respective drive paths may be next to one another. In the case of linear drive paths, the respective drive paths may be parallel to one another. In the case of curved or non-linear drive paths, the respective drive paths may maintain a constant distance to one another such that they are parallel at any individual point along the path. The respective drive paths may be determined by the structure that is driving each of the drive transfer elements 404a, 404b, 404c.

Figure 6:
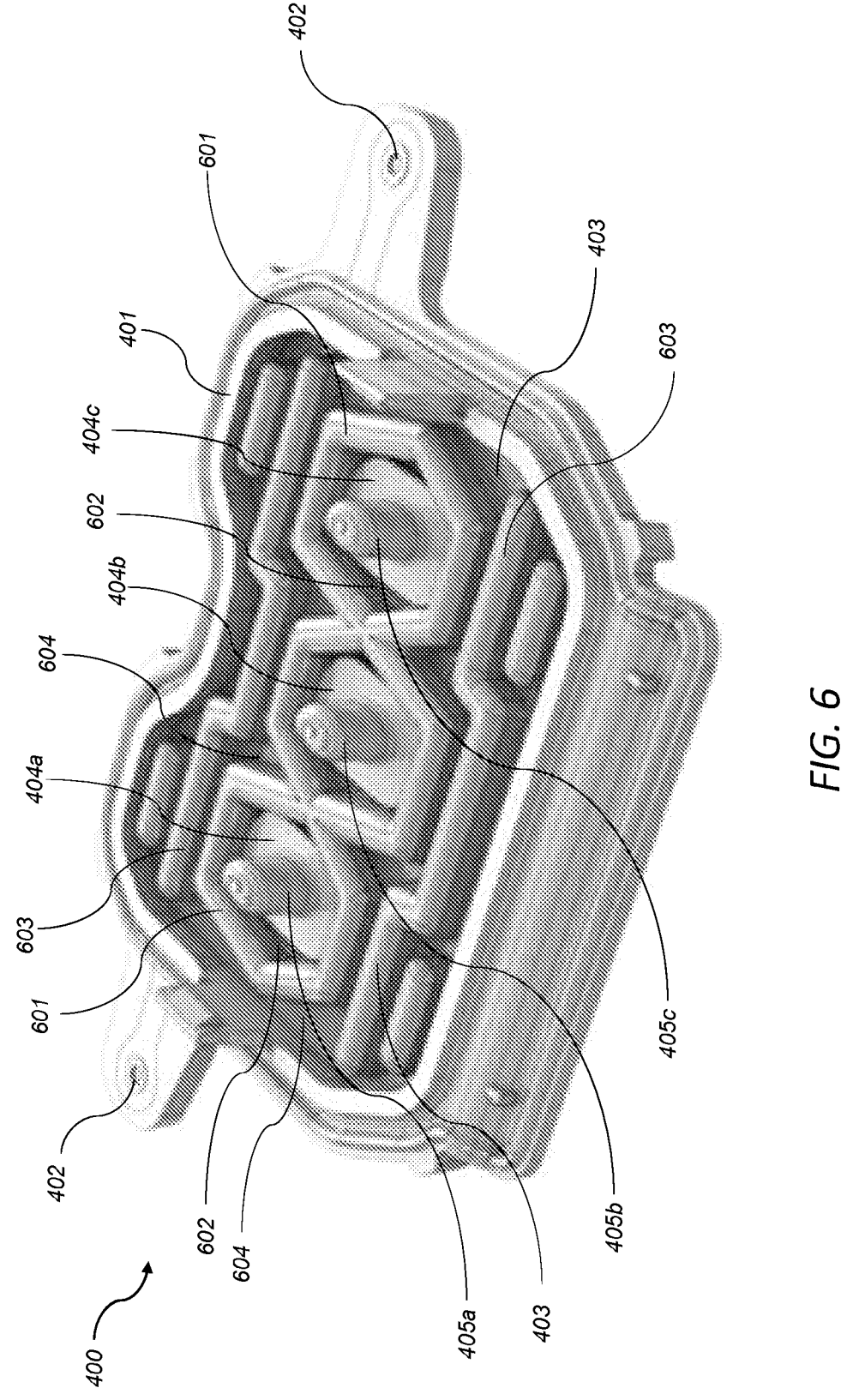
FIG. 6 illustrates a perspective view of a drape interface structure of a first embodiment.
Figure 7:
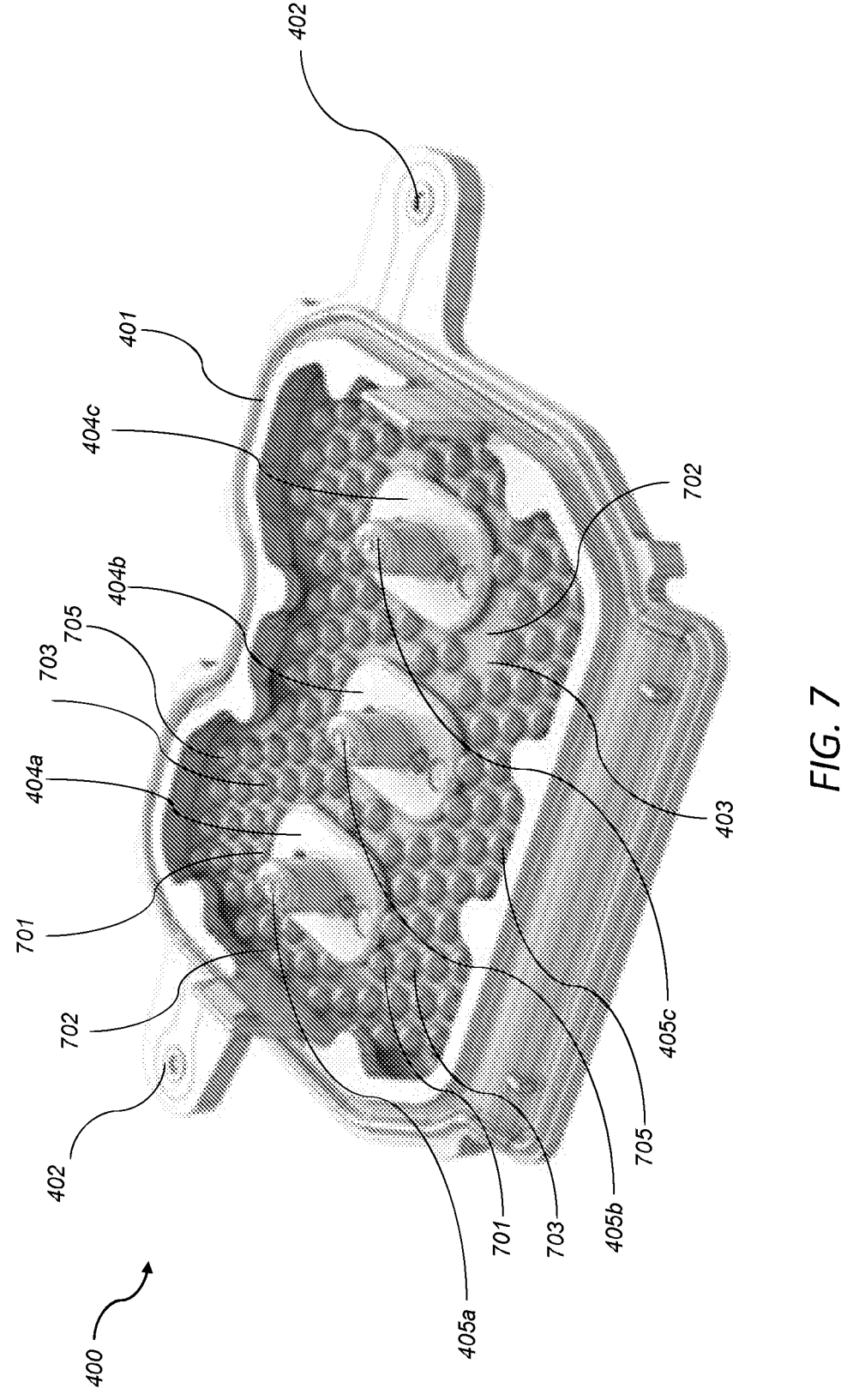
FIG. 7 illustrates a perspective view of a drape interface structure of a second embodiment.

Three possible embodiments of the invention are illustrated in FIGS. 6 to 8.

As shown in FIGS. 4 and 6 to 8, the drive transfer element 404 is surrounded by the membrane 403 and held within the membrane 403. In this way, the drive transfer element 404 may be held in an initial position. In the initial position, the drive transfer element 404 is supported by the tension in the membrane 403. The membrane 303 is in a strained state in which tensile forces from the membrane 403 hold the drive transfer element 404 in place. In implementations where the membrane 403 is planar, this may hold or support the drive transfer element 404 substantially in the plane of the membrane 403. The drive transfer element 404 preferably moves in the plane of the membrane 403, rather than out of the plane of the membrane 403. In this way, the tension in the membrane 403 may be reduced.

Any movement of the drive transfer element 404 in the membrane 403 would need to overcome the tension provided by the membrane 403. As such, driving the drive transfer element 404 in the membrane 403 would need significant force. The tension force from the membrane 403 can also be inconsistent. High and/or inconsistent tension force from the membrane 403 can add additional loading on the driving elements and can make it difficult to control the position of the driving elements. The increased loading on the drive transfer elements can also result in less cable tension in the instrument 103 for a given motor torque. Additionally, increasing the tension in the membrane 403 can increase the likelihood of tearing of the membrane 403. The tension can be particularly high when two drive transfer elements 404 are at opposite ends of travel, or are both a long way from their respective starting positions. Alternatively, tension can be particularly high in rotary drive when drive transfer elements 404 turn by a large angle. It can therefore be advantageous to reduce the level of tension in the membrane 403.

As described herein, the drive transfer element 404 can be driven within the membrane 403. As the membrane 403 is constrained by the frame 401, movements in the membrane 403 are movements relative to the frame 401. The membrane 403 comprises regions across the opening of different elastic deformability. In other words, the elastic deformability of the membrane 403 may vary across the plane of the membrane 403. Preferably, the membrane 403 is configured to only elastically deform and not to plastically deform. In particular, the membrane 403 may be configured such that the movement of the drive transfer element(s) 404 does not cause the yield stress of the membrane 403 to be exceeded. In this way, the structure of the membrane 403 may not be damaged, and the sterile barrier may not be compromised.

The membrane 403 may comprise a first region 601, 701, 801 of a first elastic deformability and a second region 602, 702, 802 of a second elastic deformability different from the first elastic deformability. The first region 601, 701, 801 may be less elastically deformable than the second region 602, 702, 802. The first region 601, 701, 801 may comprise a less deformable region 601, 701, 801. The second region 602, 702, 802 may comprise a more deformable region 602, 702, 802. There may be one or more regions which are less deformable and there may be one or more regions which are more deformable. FIGS. 6 to 8 illustrate the less deformable regions 601, 701, 801 and the more deformable regions 602, 702, 802.

A less deformable region 601, 701, 801 and a more deformable region 602, 702, 802 may be adjacent to one another. In this way, in response to movement of the drive transfer element, the more deformable region 602, 702, 802 preferably elastically deforms over the less deformable region 601, 701, 801. In other words, the more deformable region 602, 702, 802 requires less force to deform when compared to the less deformable region 601, 701, 801. As such, the more deformable region 602, 702, 802 deforms before and/or by a larger amount than the less deformable region 601, 701, 801.

The result of the preferential deformation is that the membrane 403 may deform in certain directions and/or regions more than in other directions and/or regions. This may allow the membrane 403 to apply, or provide, reduced force and/or resistance on the drive transfer element 404 in certain directions in and/or regions of the membrane 403.

As described herein, the drive transfer element 404 can be driven within the membrane 403. As the membrane 403 is constrained by the frame 401, movements in the membrane 403 are movements relative to the frame 401. Preferably, the less deformable region 601, 701, 801 and the more deformable region 602, 702, 802 are arranged such that the resistance on the movement of the drive transfer element 404 is less in a direction along the drive path than in a direction not along the drive path of the drive transfer element 404. In other words, the membrane 403 is configured to apply a lower resistance on the movement of the drive transfer element 404 in a direction along the drive path. The membrane 403 is also configured to have a higher resistance on the movement of the drive transfer element 404 in a direction not along the drive path. As a result, when the drive transfer element 404 is driven along the drive path, then the resistance from the membrane 403 is less than if the drive transfer element 404 were to be driven in a different direction which is not along the drive path. It is possible that the membrane 403 may be configured to have other directions in which resistance is at a lower level. For example, the resistance in directions close to the drive path may have similarly low resistance levels. However, the resistance in the direction of the drive path is lower than the resistance in at least one direction not in the direction of the drive path. In this way, the resistance on the drive transfer element 404 is reduced in the normal operating zone of the drive transfer element 404.

More preferably, the less deformable region 601, 701, 801 and the more deformable region 602, 702, 802 are arranged such that the resistance on the movement of the drive transfer element 404 is lowest in a direction along the drive path. In other words, the resistance on the movement of the drive transfer element 404 in the direction along the drive path is the lowest level of resistance of all of the directions within the membrane 403. In this way, the resistance on the drive transfer element 404 is at its lowest level in the normal operating zone of the drive transfer element 404. As a result of the lower resistance in the direction along the drive path, the tension force from the membrane 403 is reduced.

As an example, once the angle of the direction of the drive transfer element 404 moves away from the drive path, then the level of resistance may increase. In particular, the less deformable region 601, 701, 801 and the more deformable region 602, 702, 802 are arranged such that there is increasing resistance on the movement of the drive transfer element 404 with respect to the angle of the direction of movement of the drive transfer element 404 from the drive path. Merely by way of example, if the angle of the direction of movement of the drive transfer element 404 is 0° then it may have a lower resistance than 15°, which may in turn have a lower resistance than 30°. The increase in resistance with respect to angle of the direction of movement of the drive transfer element 404 from the drive path may increase linearly.

Alternatively, increase in resistance with respect to angle of the direction of movement of the drive transfer element 404 from the drive path may increase non-linearly, for example as defined by function of angle. The relation between the resistance and the angle of the direction of movement of the drive transfer element 404 from the drive path may depend on the arrangement of the less deformable region 601, 701, 801 and the more deformable region 602, 702, 802.

Preferably, the less deformable region 601, 701, 801 and the more deformable region 602, 702, 802 are arranged such that the highest level of resistance on the movement of the drive transfer element 404 in a direction perpendicular to the drive path. In other words, if the drive transfer element 404 is moved in a direction significantly from the drive path, then the resistance will be significantly higher. As described herein, as the level of resistance may increase with the angle of the direction of movement of the drive transfer element 404 from the drive path, the level of resistance may be a maximum in a direction 90° from the drive path. The level of resistance may increase with angle of the direction of movement of the drive transfer element 404 from the drive path between 0° and 90°. The level of resistance may decrease with angle of the direction of movement of the drive transfer element 404 from the drive path between 90° and 180°.

As shown in FIG. 5, and as described herein, the membrane 403 may comprise a thin-skinned structure. Preferably, the drive transfer element 404 is configured to be driven in the plane of the thin-skinned membrane 403. As such, the variation of the resistance with angle of the direction of movement of the drive transfer element 404 from the drive path may be in the plane of the membrane 403. For example, a movement perpendicular to the drive path would be in the plane of the membrane 303 at 90° from the drive path. However, in embodiments where the membrane 403 is not thin-skinned and/or planar, the resistance may also vary with angle of the direction of movement of the drive transfer element 404 from the drive path, in which the angle is with respect to the plane of the drive path. For example, the resistance may increase if the drive transfer element 404 moves above or below the membrane 403.

It may be advantageous to provide a lower resistance in the direction along the drive path and a higher resistance in a direction not along the drive path. For example, a lower resistance along the drive path may reduce the resistance on the drive transfer element 404 during operation, i.e., when the drive transfer element 404 is being driven along its operating path. This may reduce the loading on the driving elements which may also make it easier and more accurate to control the position of the driving element. Additionally, a higher resistance in a direction not along the drive path may force the drive transfer element 404 to be pushed back to its operating path, i.e., if the drive transfer element 404 has been displaced from the drive path. The increased loading on the driving elements from the increase resistance may also provide feedback to the control system 106 that the drive transfer element 404 is not on the operating path.

As shown in FIGS. 6 to 8, the less deformable region 601, 701, 801 may comprise a greater thickness than the more deformable region 602, 702, 802. The thickness is measured in the dimension normal to the plane of the membrane 403. As shown in FIG. 5, and as described herein, the membrane 403 may comprise a thin-skinned structure. As such, the increased thickness of the less deformable region 601, 701, 801 extends above and/or below the membrane 403.

The less deformable region 601, 701, 801 may comprise a portion attached to the membrane 403. The portion may provide the increased thickness to the less deformable region 601, 701, 801. The portion may be attached to the surface of the membrane 403. In this way, the portion may protrude from the surface of the membrane 403. The portion may be attached above and/or below the membrane 403. The portion may be heat welded to the membrane 403. The heat welding may be as described herein. Alternatively, the portion may be attached through the membrane 403.

Alternatively, or additionally, the less deformable region 601, 701, 801 may comprise a thicker region of the membrane 403 material than the more deformable region 602, 702, 802. The thickness of the membrane 403 may be increased to provide the increased thickness to the less deformable region 601, 701, 801. In other words, the increased thickness may be integral to, or a part of, the membrane 403. The increased thickness of the membrane 403 may extend above and/or below the membrane 403.

In some examples, portions may be attached to a region of increased thickness in the membrane 403 to provide the less deformable region 601, 701, 801. Attaching the portions to a thicker region of membrane 403 may make the attachment more secure.

The thicker less deformable region 601, 701, 801 may provide a stiffer structure than the thinner more deformable region 602, 702, 802. This may be because the increased thickness of the less deformable region 601, 701, 801 is more difficult to bend and/or deform when compared to the thinner more deformable region 602, 702, 802. As a result, the thinner region may deform before and more easily than the thicker region.

Alternatively, or in addition, to the thicker region, the less deformable region 601, 701, 801 may have a greater stiffness than the more deformable region 602, 702, 802. Instead of thickness, the increased stiffness may be as a result of the configuration or arrangement of the less deformable region 601, 701, 801. For example, the less deformable region 601, 701, 801 may comprise a denser structure and/or the more deformable region 602, 702, 802 may comprise a less dense structure than the rest of the membrane 403. The denser structure may be a solid structure, whereas the less dense structure may be a porous structure or comprise cavities. In these examples, it is likely that the material of the less deformable region 601, 701, 801 and the more deformable region 602, 702, 802 are the same. Constructing the membrane 403 from a single material may simplify manufacturing. Alternatively, or additionally, the material of the less deformable region 601, 701, 801 and the more deformable region 602, 702, 802 may be different. For example, the less deformable region 601, 701, 801 may comprise a stiffer material and/or the more deformable region 602, 702, 802 may comprise a less stiff material than the rest of the membrane 403. The variation in density, structure and material of the regions of the membrane 403 may be combined depending on the design requirement for the membrane 403.

As described herein with reference to FIG. 4, the drape interface structure 400 may comprise more than one drive transfer element 404. FIG. 4 shows three drive transfer elements 404a, 404b, 404c. One or more less deformable regions 601, 701, 801 and one or more deformable regions 602, 702, 802 are arranged such that the resistance on the movement of each of the drive transfer elements 404a, 404b, 404c is less in a direction along the respective drive path than in a direction not along the respective drive path. In other words, the membrane 403 is configured to have a lower resistance on the movement of the drive transfer elements 404a, 404b, 404c in a direction along the respective drive paths. The membrane 403 is also configured to have a higher resistance on the movement of the drive transfer elements 404a, 404b, 404c in a direction not along the respective drive paths. As a result, when each of the drive transfer elements 404a, 404b, 404c are driven along their respective drive paths, then the resistance from the membrane 403 is less than if each of the drive transfer elements 404a, 404b, 404c were to be driven in a different direction which is not along their respective drive path. In particular, the one or more less deformable regions 601, 701, 801 and the one or more deformable regions 602, 702, 802 are arranged such that the resistance on the movement of each of the drive transfer elements 404a, 404b, 404c is lowest in a direction along the respective drive path.

As described herein, the each of the drive transfer elements 404a, 404b, 404c may move along a respective drive path. The respective drive paths may be a linear path. The respective drive paths may be circular paths. The respective drive paths may be irregular with linear and curved sections. In this case of linear drive paths, the drive path may follow a drive axis. The respective drive paths may be next to one another. In the case of linear drive paths, the respective drive paths may be parallel to one another. In the case of curved or non-linear drive paths, the respective drive paths may maintain a constant distance to one another such that they are parallel at any individual point along the path. The respective drive paths may be determined by the structure that is driving each of the drive transfer elements 404a, 404b, 404c.

In the case of parallel drive paths, the membrane 403 may be configured to have a lower resistance in the direction of all the drive paths. In this way, each of the drive transfer elements 404a, 404b, 404c may be provided with the lower resistance. However, in embodiments in which the respective drive paths are not parallel, the direction of lower resistance may only align with one or more of the drive paths. For example, if there are three the drive transfer elements 404a, 404b, 404c each with drive paths in different directions, then the direction of lower resistance may be aligned with one of the drive transfer elements 404a, 404b, 404c. Preferably, the drive transfer element 404a, 404b, 404c selected to have the lowest resistance from the membrane 403 may be the drive transfer element 404a, 404b, 404c with the longest range of travel, or highest amount of operational use. Alternatively, the membrane 403 may be configured such that, even if the drive paths are not parallel, the membrane 403 still has a low level of resistance for each of the drive transfer elements 404a, 404b, 404c. For example, the one or more less deformable regions 601, 701, 801 and the one or more deformable region 602, 702, 802 are arranged such that a reduced level of resistance is provided to each of the drive transfer elements 404a, 404b, 404c along the respective drive paths.

A first embodiment of the invention is illustrated in FIG. 6.

As shown in FIG. 6, the more deformable region 602 encloses drive transfer element 404. The less deformable region 601 encloses the more deformable region 602. As the membrane 403 is planar, the enclosing of the different regions may be in 2D. In other words, the regions may not be enclosed above and below the membrane 403 surface in 3D. As a result, the drive transfer element 404 may relatively freely move within the less deformable region 601. In the example in FIG. 6, the drive path of the drive transfer element 404 is parallel to the shorter edge of the frame 401. As the movement of the drive transfer element 404 moves closer to the less deformable region 601, the less deformable region 601 may be pushed by the drive transfer element 404. The less deformable region 601 may therefore be designed to be longer in the direction of the drive path such that the drive transfer element 404 may move substantially within the less deformable region 601 before the less deformable region 601 is moved. As a result, the resistance on the drive transfer element 404 may be less in the direction of the drive path.

In FIG. 6, the less deformable region 601 is shown to have a hexagonal structure which is longer along the drive path of the drive transfer element 404. It will be appreciated that other structures, such as oval and rectangular structures, may also be suitable. It is preferred that the less deformable region 601 is longer in the direction of the drive path such that the resistance on the drive transfer element 404 may be less in the direction of the drive path. The more deformable region 602 is shown to surround the drive transfer element 404 and fill the less deformable region 601. The more deformable region 602 may suitably correspond to the shape of the more deformable region 601.

As shown in FIG. 6, a further more deformable region 604 encloses the less deformable region 601. A further more deformable region 604 is at least partially enclosed by a further less deformable region 603. As the membrane 403 is planar, the enclosing of the different regions may be in 2D. In other words, the regions may not be enclosed above and below the membrane 403 surface in 3D. As a result, the drive transfer element 404 and the less deformable region 601 may together relatively freely move within the further less deformable region 603. As the movement of the less deformable region 601 moves closer to the further less deformable region 603, the further less deformable region 603 may be pushed by the less deformable region 601.

The further less deformable region 603 may therefore be designed to run substantially parallel to the direction of the drive path such that the less deformable region 601 may move substantially towards the further less deformable region 603 before the further less deformable region 603 is moved. As a result, the resistance on the drive transfer element 404 may be less in the direction of the drive path.

In FIG. 6, the further less deformable region 603 is shown to have a generally linear structure, at least in the region adjacent the drive transfer element 404, which is substantially parallel to the direction of the drive path of the drive transfer element 404. It will be appreciated that other structures, such as curved or irregular structures, may be suitable. It is preferred that the further less deformable region 603 is substantially parallel to the direction of the drive path such that the resistance on the drive transfer element 404 may be less in the direction of the drive path. The further more deformable region 604 is shown to surround the drive transfer element 404 and fill between the less deformable region 601 and the further less deformable region 603. The further more deformable region 604 may suitably correspond to the shape of the further more deformable region 603. Additionally, a second further less deformable region 603 is located on the opposite end of the drive path of the drive transfer element 404. The second further less deformable region 603 may provide reduced resistance as described herein with reference to the first further less deformable region 603.

The membrane 403 may comprise more than two less deformable regions 601, 603 and more than two more deformable regions 602, 604. For example, as shown in FIG. 6, there may be further banks of further less deformable regions 603. The further banks of further less deformable regions 603 may be separated by the further more deformable regions 604. The further banks of further less deformable regions 603 may provide a reduced level of resistance over a longer drive path. As such, the drive transfer element 404 may travel further before the resistance substantially increases.

In FIG. 6, the bars 601, 603 are described to provide the less deformable regions 601, 603. For example, the bars 601, 603 may provide the less deformable regions 601, 603 by being thicker or stiffer, as described herein, than the surrounding membrane 403. In an alternative embodiment, the bars 601, 603 may comprise corrugations, and/or other flexible structures, and so provide the more deformable regions 602, 604. In this case, the bars 601, 603 may be more deformable than the surrounding membrane 403.

As described herein with reference to FIG. 4, the drape interface structure 400 may comprise more than one drive transfer element 404. FIG. 4 shows three drive transfer elements 404*a*, 404*b*, 404*c*. FIG. 6 shows a single less deformable region 601 which individually encloses each of the drive transfer elements 404*a*, 404*b*, 404*c* in respective more deformable regions 602. Alternatively, the less deformable region 601 may enclose each of the drive transfer elements 404*a*, 404*b*, 404*c* in a single more deformable region 602. As the membrane 403 is planar, the enclosing of the different regions may be in 2D. In other words, the regions may not be enclosed above and below the membrane 403 surface in 3D. Alternatively, there may be a deformable region 601 for each of the respective drive transfer elements 404*a*, 404*b*, 404*c*. Preferably, the less deformable region 601 provides sufficient length for each of the drive transfer elements 404*a*, 404*b*, 404*c* to move within the less deformable region 602 with minimal resistance.

FIG. 6 shows a single further less deformable region 603 on either side of the drive path of each of the drive transfer elements 404*a*, 404*b*, 404*c*. Alternatively, there may be more than one further less deformable region 603 for each of the respective drive transfer elements 404*a*, 404*b*, 404*c*. Preferably, the further less deformable region 603 is substantially perpendicular to the respective drive paths such that each of the drive transfer elements 404*a*, 404*b*, 404*c* move within the further less deformable region 604 with minimal resistance.

An arrangement where the less deformable region 601 is longer in the direction of the drive path for each of the drive transfer elements 404, and/or the further less deformable region 603 is substantially parallel to the direction of the drive path, may be particularly beneficial in embodiments where the drape interface structure 400 also comprises more than one drive transfer element 404 with adjacent drive paths. This is because, the arrangement may allow the membrane 403 to cope with the extreme tension caused by adjacent drive transfer elements 404 being at opposite ends of their respective drive paths.

A second embodiment of the invention is illustrated in FIG. 7.

As shown in FIG. 7, a plurality of less deformable regions 701 at least partially surround the drive transfer element 404. Preferably, there are sufficient drive less deformable regions 701 so as to substantially surround the drive transfer element 404. The plurality of less deformable regions 701 and the drive transfer element 404 are separated by the more deformable region 702. As a result, the drive transfer element 404 may relatively freely move within the closest less deformable regions 701. In the example in FIG. 7, the drive path of the drive transfer element 404 is parallel to the shorter edge of the frame 401. As the movement of the drive transfer element 404 moves closer to the less deformable regions 701 that are closest in the direction of the drive path, the less deformable regions 701 may be pushed by the drive transfer element 404. The less deformable regions 701 may therefore be designed to be spaced from the drive transfer element 404 such that the drive transfer element 404 may move substantially within the less deformable regions 701 before the less deformable regions 701 are moved. As a result, the resistance on the drive transfer element 404 may be less in the direction of the drive path.

As shown in FIG. 7, farther less deformable regions 703 substantially surround the closest less deformable regions 701. The more deformable region 702 separates the farther less deformable regions 703 and the closest less deformable regions 701. As a result, the drive transfer element 404 and the closest less deformable regions 701 may together relatively freely move within the farther less deformable regions 703. As the movement of the closest less deformable regions 701 move closer to the farther less deformable regions 703, the farther less deformable regions 703 may be pushed by the closest less deformable regions 701. The farther less deformable regions 703 may therefore be designed to run substantially parallel to the direction of the drive path such that the drive transfer element 404 may move substantially towards the farther less deformable regions 703 before the farther less deformable regions 703 are moved. As a result, the resistance on the drive transfer element 404 may be less in the direction of the drive path.

In FIG. 7, the less deformable regions 701, 703 are shown to be arranged in a hexagonal pattern around the drive transfer element 404. The hexagonal pattern provides a means for the less deformable regions 701, 703 to slot between one another when the separating more deformable region 702 is deformed. As such, the membrane 403 may provide a lower level of resistance in the direction symmetrically intersecting the hexagonal shape. Preferably, the drive path is aligned with a direction that symmetrically intersects the hexagonal shape such that the level of resistance is a minimum. It will be appreciated that other patterns, such as triangular and rectangular structures, may be suitable. It is preferred that the pattern provides a means for the less deformable regions 701, 703 to slot between one another when the more deformable region 702 is deformed.

The membrane 403 may comprise additional less deformable regions 705 surrounding the farther less deformable regions 703. For example, as shown in FIG. 7, there may be further rings of additional less deformable regions 705. The further rings of additional less deformable regions 705 may be separated by the more deformable region 702. The further rings of additional less deformable regions 705 may provide a reduced level of resistance over a longer drive path. As such, the drive transfer element 404 may travel further before the resistance substantially increases.

In FIG. 7, the dimples 701, 703 are described to provide the less deformable regions 701, 703. For example, the dimples 701, 703 may provide the less deformable regions 701, 703 by being thicker or stiffer, as described herein, than the surrounding membrane 403. In an alternative embodiment, the dimples 701, 703 may comprise corrugations, and/or other flexible structures, and so provide the more deformable regions 702, 704. In this case, the dimples 701, 703 may be more deformable than the surrounding membrane 403.

As described herein with reference to FIG. 4, the drape interface structure 400 may comprise more than one drive transfer element 404. FIG. 4 shows three drive transfer elements 404a, 404b, 404c. FIG. 7 shows that the plurality of less deformable regions 701, 703, 705 at least partially surround each of the drive transfer elements 404a, 404b, 404c. Preferably, the less deformable regions 701, 703, 705 are arranged around each of the drive transfer elements 404a, 404b, 404c as described herein so as to provide the reduced level of resistance in the direction of the respective drive paths. FIG. 7 shows that each of the drive transfer elements 404a, 404b, 404c are arranged such that the respective drive paths are aligned with a direction that symmetrically intersects the hexagonal shape such that the level of resistance is a minimum.

Figure 8A:
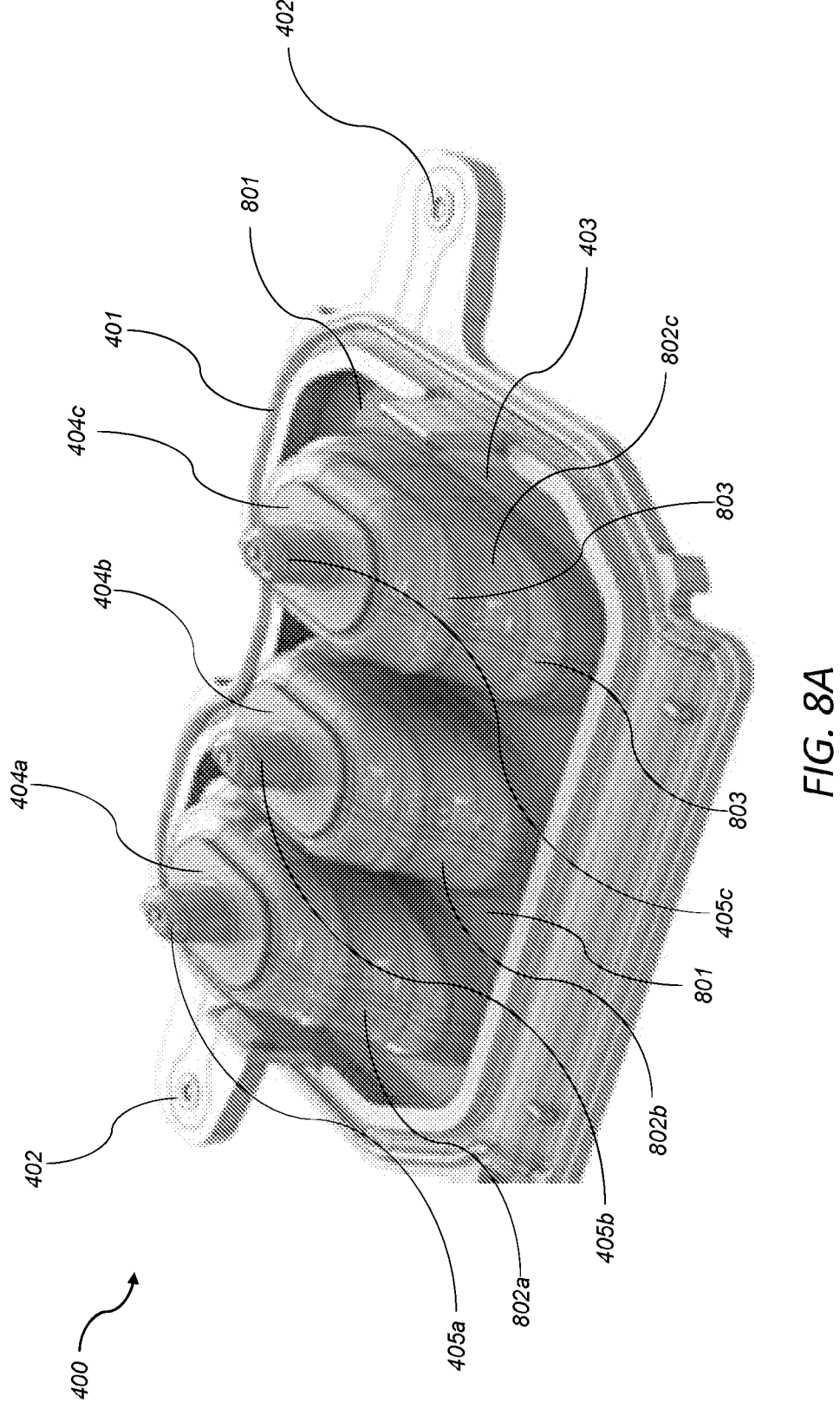
FIG. 8A illustrates a perspective view of a drape interface structure of a third embodiment.
Figure 8B:
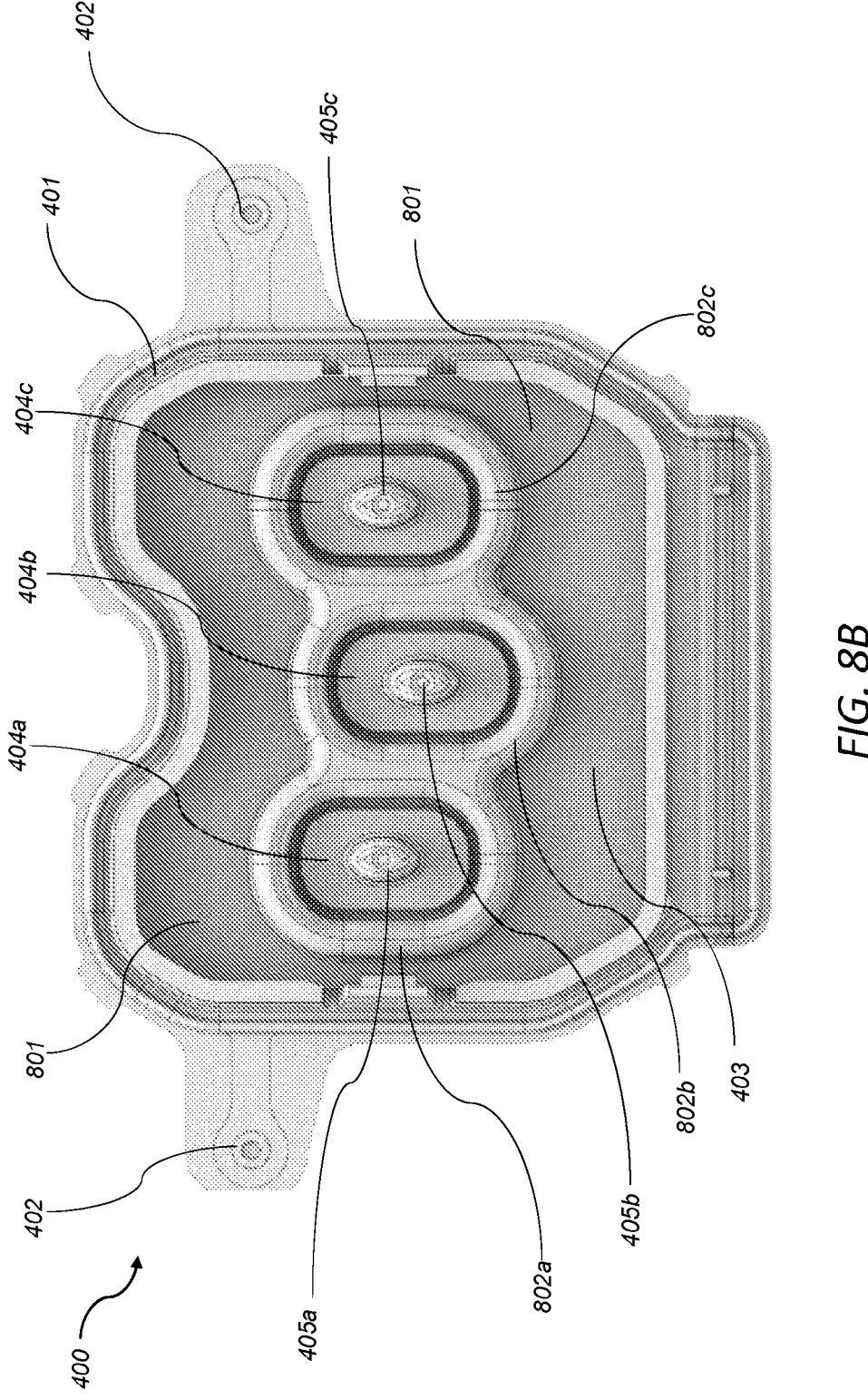
FIG. 8B illustrates a plan view of a drape interface structure of the third embodiment.

A third embodiment of the invention is illustrated in FIGS. 8A and 8B.

As shown in FIG. 8A, the more deformable region 802 comprises a corrugated structure 802. The corrugated structure 802 at least partially surrounds the drive transfer element 404. Preferably, the corrugated structure 802 fully surrounds and encloses the drive transfer element 404. The corrugated structure 802 is enclosed by the less deformable region 801. As the membrane 403 is planar, the enclosing of the different regions may be in 2D. In other words, the regions may not be enclosed above and below the membrane 403 surface in 3D. As a result, the drive transfer element 404 may relatively freely move within corrugated structure 802. In the example in FIG. 8A, the drive path of the drive transfer element 404 is parallel to the shorter edge of the frame 401. As the movement of the drive transfer element 404 moves closer to the surrounding less deformable region 801, the less deformable region 801 may be pushed by the drive transfer element 404. The corrugated structure 802 may therefore be designed to be longer in the direction of the drive path such that the drive transfer element 404 may move substantially within corrugated structure 802 before the less deformable region 801 is moved. As a result, the resistance on the drive transfer element 404 may be less in the direction of the drive path.

The corrugated structure 802 may be provided by a 'pop-up' arrangement. FIG. 8A shows the pop-up arrangement in the extended configuration. The pop-up arrangement is configured such that when it is pushed from above, the pop-up arrangement will change into a contracted configuration. The corrugated structure 802 is provided when the pop-up structure is in the contracted configuration, as shown in FIG. 8B. By changing the pop-up structure into the contracted configuration, the more deformable region 802 of the membrane 403 folds up to form the corrugated structure 802. It will be appreciated that other structures, such as a pre-set corrugation or a drawstring corrugation, may be suitable for forming the corrugated structure 802.

As shown in FIG. 8B, the corrugated structure 802 comprises one or more folds. As the drive transfer element 404 moves within the corrugated structure 802, the folds are pushed together on one side of the drive transfer element 404 and pulled apart on the other side of the drive transfer element 404. As is pushing together, and pulling apart, of the folds requires significantly less force than pushing against a tight membrane 403, the corrugated structure 802 may provide the more deformable region 802 with less resistance.

As shown in FIG. 8A, the corrugated structure 802 comprises one or more further less deformable regions 803. The further less deformable regions 803 are arranged within the corrugated structure 802. In particular, the further less deformable regions 803 fully surround the drive transfer element 404. By fully surrounding the drive transfer element 404, such as with rings, the further less deformable regions 803 may break up the more deformable region 802 within the corrugated structure 802. FIG. 8A shows two rings of further less deformable regions 803 which results in three sections of the more deformable region 802 located on either side of the rings. It will be appreciated that a different number of rings may be suitable depending on the design requirements.

As a result of the further less deformable regions 803, the drive transfer element 404 may relatively freely move within the further less deformable region 803 (ring 1). As the movement of the drive transfer element 804 moves closer to the further less deformable region 803 (ring 1), the further less deformable region 803 may be pushed by the drive transfer element 404. Once ring 1 has been pushed by the drive transfer element 804, ring 1 may move towards ring 2 and begin to push ring 2. The same may apply to further rings as the drive transfer element 404 continues to move further along the drive path.

By breaking up the more deformable region 802 with further less deformable regions 803, the distance each section of the more deformable region 802 needs to be deformed, stretched or compressed, is reduced. Reducing the amount of deformation can reduce the level of resistance on the drive transfer element 404. The more deformable region 802 may therefore be designed to be broken up in the direction of the drive path such that the drive transfer element 404 may move substantially in the more deformable region 802 before a section of the more deformable region 802 significantly deforms. As a result, the resistance on the drive transfer element 404 may be less in the direction of the drive path.

As described herein with reference to FIG. 4, the drape interface structure 400 may comprise more than one drive transfer element 404. FIG. 4 shows three drive transfer elements 404*a*, 404*b*, 404*c*. FIG. 8A shows a three corrugated structures 802*a*, 802*b*, 802*c* which respectively enclose each of the drive transfer elements 404*a*, 404*b*, 404*c*. Alternatively, a single corrugated structure 802 may enclose each of the drive transfer elements 404*a*, 404*b*, 404*c*. As the membrane 403 is planar, the enclosing of the different regions may be in 2D. In other words, the regions may not be enclosed above and below the membrane 403 surface in 3D. Preferably, the three corrugated structures 802*a*, 802*b*, 802*c* provide sufficient length for each of the drive transfer elements 404*a*, 404*b*, 404*c* to move within the respective corrugated structures 802*a*, 802*b*, 802*c* with minimal resistance.

To further reduce the resistance on the drive transfer elements 404*a*, 404*b*, 404*c* from the membrane 403, the length of the drive paths, compared to distance between adjacent drive paths may be minimized. Preferably, the length of each of the adjacent drive paths is less than five times the distance between the adjacent drive paths. Similarly, to further reduce the resistance on the drive transfer elements 404*a*, 404*b*, 404*c* from the membrane 403, the length of the drive paths, compared to distance between the frame 401 and the adjacent drive transfer element may be minimized. Preferably, the length of each of the adjacent drive paths is less than five times the distance between the frame 401 and the adjacent drive path. As a result of both options, there may be a larger area of membrane 403 which is able to stretch between the drive transfer element 404 and the adjacent component (the adjacent drive transfer element 404 or the frame 401) to which the drive transfer element 404 is moving relative. This may reduce the resistance on the drive transfer element 404.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description, it will be evident to a person skilled in the art that various modifications may be made within the scope of the invention.

The invention claimed is:

1. A drape interface structure comprising:
a rigid frame defining an opening;
a membrane spanning the opening of the frame; and
a drive transfer element attached to the membrane and adapted to convey motion through the membrane;
wherein the membrane comprises a first region of a first elastic deformability and a second region of a second elastic deformability different from the first elastic deformability, the first region comprising a less deformable region and the second region comprising a more deformable region such that, in response to movement of the drive transfer element, the more deformable region preferentially elastically deforms over the less deformable region; and
wherein the drive transfer element is adjacent to the more deformable region, the more deformable region is adjacent to the less deformable region, the less deformable region is not adjacent to the drive transfer element, and the more deformable region is between the drive transfer element and the less deformable region.

2. A drape interface structure as claimed in claim 1, wherein the less deformable region is thicker than the more deformable region.

3. A drape interface structure as claimed in claim 2, wherein the less deformable region comprises a portion attached to a surface of the membrane, and optionally wherein the less deformable region comprises a thicker region of the membrane than the more deformable region.

4. A drape interface structure as claimed in claim 1, wherein the more deformable region encloses the drive transfer element, and the less deformable region encloses the more deformable region.

5. A drape interface structure as claimed in claim 4, wherein the less deformable region is enclosed by a further more deformable region, and the further more deformable region is at least partially enclosed by a further less deformable region.

6. A drape interface structure as claimed in claim 1, wherein a plurality of less deformable regions at least partially surround the drive transfer element, and the plurality of less deformable regions and the drive transfer element are separated by the more deformable region.

7. A drape interface structure as claimed in claim 6, wherein the plurality of less deformable regions are arranged in a hexagonal pattern.

8. A drape interface structure as claimed in claim 1, comprising one or more further drive transfer elements, each further drive transfer element being attached to the membrane and adapted to convey motion through the membrane, and optionally wherein the one or more further drive transfer elements are adapted to convey motion through the membrane along respective drive paths, and the respective drive paths of the drive transfer elements are parallel to one another.

9. A drape interface structure as claimed in claim 8, wherein the more deformable region and the less deformable region are arranged so as to apply less resistance to the movement of each of the drive transfer elements in a direction along a respective drive path of each drive transfer element than in a direction not along the respective drive path, and optionally wherein the more deformable region and the less deformable region are arranged so as to apply the lowest resistance to the movement of each of the drive transfer elements in a direction along the respective drive path.

10. A drape interface structure as claimed in claim 1, wherein a material of the drive transfer element comprises a non-elastomeric material.

11. A drape interface structure as claimed in claim 10, wherein the material of the drive transfer element and/or a material of the frame comprises polyethylene.

12. A drape interface structure as claimed in claim 1, wherein the more deformable region and the less deformable region are arranged so as to apply less resistance to the movement of the drive transfer element in a direction along a drive path of the drive transfer element than in a direction not along the drive path, and optionally wherein the more deformable region and the less deformable region are arranged so as to apply the lowest resistance to the movement of the drive transfer element in a direction along the drive path.

13. A drape interface structure as claimed in claim 1, wherein the less deformable region has a greater stiffness than the more deformable region, and optionally wherein the less deformable region comprises a material with a greater stiffness than a material of the more deformable region.

14. A drape interface structure as claimed in claim 1, wherein the more deformable region comprises a corrugated structure at least partially surrounding the drive transfer element, the corrugated structure being enclosed by the less deformable region, and optionally wherein the corrugated structure comprises further less deformable regions arranged within the corrugated structure.

15. A drape interface structure as claimed in claim 1, wherein the drive transfer element comprises a recess on a first side of the membrane and a protrusion on a second side of the membrane, and optionally wherein the drive transfer element recess is engageable with an interface protrusion, and the drive transfer element protrusion is engageable with an interface recess.

16. A drape interface structure as claimed in claim 1, wherein the frame comprises a securing fitting configured to secure the frame to a robot arm.

17. A drape interface structure as claimed in claim 1, wherein the drive path of the drive transfer element is linear.

18. A drape interface structure as claimed in claim 1, wherein the rigid frame and the drive transfer element are heat welded to the membrane.

19. A drape interface structure as claimed in claim 1, wherein a material of the membrane is a thermoplastic polymer, and optionally wherein the thermoplastic polymer material of the membrane comprises one or more of high-density polyethylene or linear low-density polyethylene.

\* \* \* \* \*